US010943696B2

(12) United States Patent
Demestichas et al.

(10) Patent No.: US 10,943,696 B2
(45) Date of Patent: Mar. 9, 2021

(54) SYSTEM AND METHOD FOR PERSONALIZED MIGRAINE PREDICTION POWERED BY MACHINE LEARNING

(71) Applicant: WINGS ICT Solutions Ltd., Athens (GR)

(72) Inventors: Panagiotis Demestichas, Athens (GR); Aimilia Bantouna, Athens (GR); Eleni Giannopoulou, Athens (GR); Ioannis Stenos, Athens (GR); Vera Alexandra Stavroulaki, Athens (GR)

(73) Assignee: WINGS ICT Solutions Ltd., Athens (GR)

( * ) Notice: Subject to any disclaimer, the term of this patent is extended or adjusted under 35 U.S.C. 154(b) by 806 days.

(21) Appl. No.: 15/720,786

(22) Filed: Sep. 29, 2017

(65) Prior Publication Data

US 2018/0096107 A1    Apr. 5, 2018

Related U.S. Application Data

(60) Provisional application No. 62/402,176, filed on Sep. 30, 2016.

(51) Int. Cl.
| | |
|---|---|
| *G16H 50/20* | (2018.01) |
| *G06N 20/00* | (2019.01) |
| *G16H 50/50* | (2018.01) |
| *G16H 15/00* | (2018.01) |

(Continued)

(52) U.S. Cl.
CPC ............ *G16H 50/20* (2018.01); *G06N 20/00* (2019.01); *G16H 15/00* (2018.01); *G16H 50/30* (2018.01); *G16H 50/50* (2018.01); *G16H 50/70* (2018.01)

(58) Field of Classification Search
None
See application file for complete search history.

(56) References Cited

U.S. PATENT DOCUMENTS

| | | |
|---|---|---|
| 8,241,211 B2 | 8/2012 | Stupp et al. |
| 2003/0144829 A1 | 7/2003 | Geatz et al. |

(Continued)

OTHER PUBLICATIONS

Chawla et al, Bringing Big Data to Personalized Healthcare: A Patient-Centered Framework (Year: 2013).*

(Continued)

*Primary Examiner* — Li B. Zhen
*Assistant Examiner* — Mikayla Chubb
(74) *Attorney, Agent, or Firm* — Lessani Law Group, PC

(57) ABSTRACT

The present disclosure relates to a system, method, and computer program for predicting migraines using machine learning. More specifically, the system predicts the likelihood that a user will have a migraine within a certain period of time (e.g., a month) based on migraine causes/triggers $X_{1...n}$ identified from a migraine pattern built using deep neural networks. The system collects data from the user with respect to his/her profile, his/her migraine incidents (having experienced a migraine or not) and his/her daily habits. Based on these data, it creates the user's migraine pattern and combines this pattern with the migraine patterns from similar users (when necessary). As a result, it is able to predict the probability of getting a migraine within a period of time.

21 Claims, 9 Drawing Sheets

Example System Architecture

(51) Int. Cl.
　　　*G16H 50/30*　　　(2018.01)
　　　*G16H 50/70*　　　(2018.01)

(56) References Cited

U.S. PATENT DOCUMENTS

2016/0283686 A1* 9/2016 Hu ........................ G06N 5/003
2020/0143922 A1* 5/2020 Chekroud ............ G06K 9/6218

OTHER PUBLICATIONS

Cherif et al, SOM time series clustering and prediction with recurrent neural networks (Year: 2011).*
Kuremoto et al, Parameterless-Growing-SOM and Its Application to a Voice Instruction Learning System (Year: 2010).*
Lipton et al, Learning to Diagnose with LSTM Recurrent Neural Networks (Year: 2016).*
International Search Report in PCT Application No. PCT/IB2017/056028 dated Jan. 19, 2018.
Written Opinion of the International Searching Authority in PCT Application No. PCT/IB2017/056028 dated Jan. 19, 2018.
Written Opinion of the International Preliminary Examining Authority in PCT Application No. PCT/IB2017/056028 dated Aug. 29, 2018.

* cited by examiner

Inputs and Outputs of Prediction Subsystem

Construction of the Self-Organized Map (based on user profile data) that classifies the users and depicts the associations between users with similar profiles.

Users provide their profile information

Users log their daily habits and migraine incidents

The personalized probability to experience a migraine is conveyed to each user through a user interface User's feedback is required in cases when the migraine risk was high but a migraine incident has not been registered

SYSTEM AND METHOD FOR PERSONALIZED MIGRAINE PREDICTION POWERED BY MACHINE LEARNING

RELATED APPLICATIONS

This application claims the benefit of U.S. Provisional Application No. 62/402,176, filed on Sep. 30, 2016, and titled "System and Method for Personalized Migraine Prediction Powered by Artificial Intelligence," the contents of which are incorporated by reference herein as if fully disclosed herein.

BACKGROUND ART

1. Field of the Invention

This disclosure relates generally to preventative data analytics and, more specifically, personalized migraine prediction.

2. Description of the Background Art

Migraines are intense headache attacks that last from 4 to 72 hour (if not treated) and are among the eight most disabling diseases based on World Health Organization (WHO). They affect almost 15% of the world population and impact their personal lives, productivity and work relationships, but still are not adequately treated. This is highly related to the fact that there are seven categories of migraine triggers that may apply in different combinations in the same person. Last but not least, the people who suffer from migraines usually spend more money in healthcare than those who don't ($60 higher average monthly healthcare costs).

Currently, they are either self-treated (i.e., the migraineur takes over-the-counter medication/painkillers, make some actions that he/she has identified to relieve his/her pain, etc.) or with the help of expertized doctors (e.g., neurologists), who collect information from the patient, using questionnaires and migraine diaries, and try to identify the type of medication that best fits into his/her condition (i.e., preventative or acute treatment, different types of medication and dosology). Apart from the above, there are also available some mobile applications. These may be related to migraines as:

- applications that identify the triggering factors of the user or predict a non-personalized migraine "burst" e.g., due to weather;
- diaries, i.e., applications where the user can keep track of his/her migraines, the context under which they occurred and the symptoms—similarly to the hard-copied diaries that the doctors ask their patients to fill in;
- diaries of migraine triggers (e.g., food habits) where migraines are only stated as symptoms
- mobile applications that can help you relax using melodies or acupressure and thus relieve yourself from the pain of the migraine.

One of the main problems with migraines, that influence their adequate treatment, is that they are usually underestimated, and thus 50% of people who suffer from migraines prefer self-treatment than visit a doctor. However, they do not have the necessary experience or tools. Moreover, the diversity of the triggering factors and their combinations make it difficult to predict the next migraine attack and apply personalized treatment. The offered applications listed above either do not provide any insight to the user, i.e., the user needs to analyze his/her data himself/herself (e.g., diary applications), or they need a period of 45-90 days to identify the migraine triggers (e.g., Currelator, Migraine Coach) or the insights they provide is not personalized (e.g., Migraine Radar).

Predicting the next migraine incident is not dealt within any of the currently-available migraine applications. However, predicting the next migraine a) may help migraineurs schedule their activities based on their foreseen condition (limiting the need for re-scheduling during or after the migraine) or b) allow them avoid the next incident (or at least limit the intense of the next incident) by avoiding the triggering factors of their migraines and receiving their medication on time, i.e., at the beginning of the migraine incidents. According to the doctors, the sooner you receive a meditation during a migraine, the better its performance.

SUMMARY OF THE DISCLOSURE

This disclosure relates to a system and method for predicting migraines using machine learning. The methods described herein are performed by a computer system (referred to herein as "the system"). In one embodiment, the system comprises: (1) a backend prediction subsystem (comprising one or more servers) that creates patterns and performs the prediction analysis, (2) a client GUI application on a client computing device (e.g., a mobile application on a mobile phone) that provides a user interface for the user, and (3) a storage module for storing user input data. Via a user interface provided by the client GUI application, the system obtains user profile information from a plurality of users. The system clusters users into groups based on the similarity of their user profile information. In one embodiment, the system, supported by a Parameterless Growing Self-Organizing Map (PLGSOM) technique, creates a SOM neural map to cluster users. Each time a new user registers, a new SOM is created with all the previously-registered users and the new user.

The system also obtains daily information and migraine incident reports from users over a period of time. For each user, the system applies Deep Learning-based heuristics to the daily information and migraine reports to build a plurality of patterns that each describe under which circumstances (i.e., combination of values for the "daily information" parameters (see Table 3), time-based occurrence of these circumstances, etc.) the user experiences migraine attacks. These patterns are then exploited by the system so as identify how close to meeting these circumstances the user is and thus to predict the likelihood of a user having a migraine event within a certain period of time (e.g., a month) based on migraine causes/triggers $X_{1...n}$, identified from the migraine patterns. A prediction is triggered by receipt of a new daily information report from a user. A prediction may be based solely on the user's data or it may be based on a combination of the user' data and similar user's data, as determined by configuration management algorithms that periodically evaluate the performance of the prediction system. Any false positive feedback from a user is used to retrain the system for the user. This is repeated on an asynchronous and daily basis.

DETAILED DESCRIPTION OF THE PREFERRED EMBODIMENTS

Figure 1:
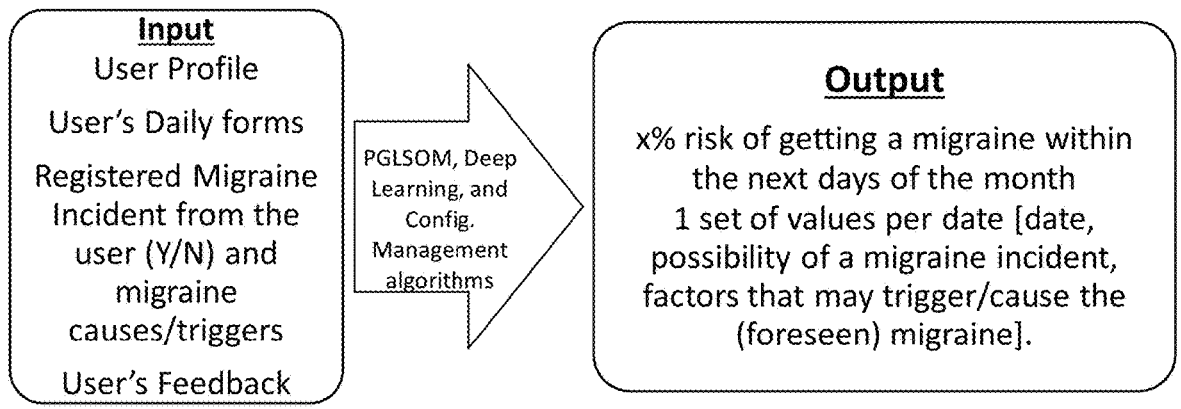
FIG. 1 is a block diagram that illustrates the inputs and outputs of a prediction subsystem according to one embodiment.

The present disclosure relates to a system and method for predicting migraines using machine learning. More specifically, the system predicts the likelihood that a user will have a migraine within a certain period of time (e.g., a month) based on migraine causes/triggers $X_{1...n}$ identified from a migraine pattern built using deep neural networks.

The system collects data from the user with respect to his/her profile (e.g., see Table 1), his/her migraine incidents (having experienced a migraine or not) and his/her daily habits (e.g., see Table 3). Based on these data, it creates the user's migraine pattern and combines this pattern with the migraine patterns from similar users (when necessary). As a result, it is able to predict the probability of getting a migraine within the month so as to allow the user to better schedule his/her activities and minimize the impact in his/her personal and professional life. The probability of a migraine incident is offered on a daily basis while an overview of the migraine risk can be accessed on a month overview. In order to deal with the diversity of the factors that can cause a migraine and to be able to predict the user's next migraine incident, inputs from the user's information are combined with machine learning algorithms, including Deep Learning techniques, in order to build a powerful subsystem.

1. User Input into the System

The system obtains profile information, daily information, and migraine incident information from numerous users to train the system and make predictions. In one embodiment, these inputs are entered via a Profile form, Migraine Incident form, and the Daily Information form, as described in more detail below.

Table 1 illustrates an example of the type of information requested in the Profile form. In this case, the Profile information is organized to seven separate sub-sections: a) "Profile Information", b) "Doctor Information", c) "Environmental Information", d) "Physiological Information", e) "Dietary Habits", f) "Medical Information" and g) "Migraine Information" so as to facilitate the user's answers.

Table 2 illustrates an example of the type of information requested in the Migraine Incident form. In this case, the Migraine Incident information is organized in three different sub-sections: a) "Description", b) "Symptoms" and c) "Actions Taken". The migraine incident information is minimal due to the fact that it is best to limit the information requested by the user when he/she is in pain, i.e., during a migraine incident.

The Daily Form information is highly related to the prediction of the probability the user to experience a migraine incident within the month. This information is used in order to get insights about a user's daily habits. Utilizing this information on a daily basis, the system predicts the probability of a specific user to experience a migraine incident. Table 3 illustrates an example of the type of information requested in the Daily Information form. This information is organized to four different sections: a) "Physical Conditions", b) "Eating Habits", c) "Environmental Aspects" and d) "Medical Aspects".

As stated above (and described in more detail below), the system includes a prediction subsystem that takes as input the information presented above, concerning a user's Profile, Incident and Daily Habits (e.g., see Tables 1-3). The user's daily habits are either fed directly to the prediction subsystem or are complemented with data from other users that have a similar profile. The prediction subsystem subsequently uses this information in order to foresee the probability of a specific user to get a migraine attack within the month (or other time period) based on the user's migraine causes/triggers $X_{1...n}$, as identified from the user's migraine pattern.

Tables 1-3 are set forth below.

TABLE 1

Inputs from Profile Information

| | Information Type | Specifications |
|---|---|---|
| Profile Information | Sex | The user selects either male or female. |
| | Menopause | Only for female users. The user selects if she is in menopause |
| | Birth Date | The user selects the year of his/her birth date |
| | Weight | The user inserts his/her weight as a decimal number. |
| | Height | The user inserts his/her height as a decimal number. |
| | Physical activities Frequency | The user selects the frequency he/she exercises: a) None, b) 1 to 2, c) 3 to 5 and d) more than 5 (4-dimension parameter). |
| Doctor Information | Doctor | The user provides information regarding the doctor he/she is being advised by and his/her real contact information so as to allow the doctor to confirm that he/she is his patient. |
| | Send data to doctor | The user confirms that he/she wants to share this information with his/her doctor |
| Environmental Information | User's address | The user can enter his/her location. |
| | Humidity level | The user selects among the values of a) low, b) medium and c) high. |
| | Noise level | The user selects among the values of a) low, b) medium and c) high. |
| | Pollution level | The user selects among the values of a) low, b) medium and c) high. |
| | Lighting level | The user selects among the values of a) low, b) medium, and c) high. |

TABLE 1-continued

Inputs from Profile Information

| Information Type | | Specifications |
|---|---|---|
| Physiological Information | User's profession | The user selects among a) a list of specific professions (e.g., accountant, bricklayer, dentist, etc.), b) other: office work in the case that he/she is an office employee but his/her profession is not listed and c) other: physical work in the case that his/her work involves physical activity but his/her profession is not listed. The total number of choices (and thus the dimensions) related to the user's profession is 60. |
| | Work Time | The user selects among the values of a) day, b) night and c) shifting hours (3-dimension variable). |
| | Working hours | The user selects the number of hours he/she works per day. |
| | Sleeping habits | The user selects the number of hours he/she sleeps per night. |
| Dietary Habits | Dietary habits | The user selects among the values of a) Mostly Meat, b) Vegetarian, c) Balanced, d) Rich in saturated fat, e) High Alcohol consumption (especially red wine), f) Long periods of fasting and g) Sweets/sugar containing refreshments (7-dimension variable). |
| Medical Information | Medical conditions | The user may select between a) eye problems, b) neck problems, c) hormonal disorders, d) sleeping disorders, e) depression, f) anxiety disorders, g) rheumatologic diseases, h) bruxism and i) psychiatric conditions (9-dimension variable). |
| Migraine information | Family Migraine history | The user can select either yes or no. |
| | Headache/Migraine history | The user selects how old he/she was when his/her migraines started. |
| | Average days in pain | The user can select how many days on average he/she was in pain the previous 3 months. |
| | Migraine aura | The user can select either yes or no (if his/her migraines usually include an aura or not). |
| | Acute treatment | The user can select either yes or no (if he/she is currently taking acute treatment or not). |
| | Physician diagnosis | The user can select either yes or no (if a physician has made a diagnosis or not). |
| | Preventative treatment (current) | The user can select either yes or no (if he/she is currently taking preventative treatment or not). If the user chooses yes he/she can fill in the medication and the quantity he/she receives. |
| | Preventative treatment (past) | The user can select either yes or no (if he/she has taken preventative treatment in the past or not). If the user chooses yes he/she can fill in the medication and the quantity he/she receives. |
| | Neurostimulator | The user can select either yes or no (if he/she is using a neurostimulator to prevent migraines or not). |

TABLE 2

Inputs from Incident Information

| Information Type | | Specifications |
|---|---|---|
| Description | Ongoing event | The user indicates whether the migraine event is ongoing or not. |
| | Start date/time | The user enters the date and the time the event started. |
| | End date/time | The user enters the date and the time the event ended (Enabled only when the incident is not declared as ongoing). |
| | Pain Intensity | The user informs about the intensity of his/her pain on a scale of 1 to 10 (10 being the most intense pain). |
| | Work hours | The user provides information regarding the hours he/she has worked the day of the migraine attack. |
| | Noise exposure | The user states if he/she has been exposed to noise and (if yes) how many hours he has been exposed to this noise |
| | Other medical condition | The user states if he/she has experienced any other medical condition within the day and (if yes) what it was about. |
| | Menstruation | If the user is female, then she needs to confirm the day of her menstruation cycle. |
| Symptoms | Center of the pain | The user selects where his/her pain is located (16-dimension variable) |
| | Pain interrupted sleep | The user indicates whether the migraine pain interrupted his/her sleep or not. |
| | Aura | The user indicates whether there was an aura before the pain or not. |
| | Work/activity interruption | The user indicates how much the pain he/she experienced affected his/her work/activity on a scale of 1 to 5 (1- none, 5-very much). |
| | Nausea/Vomit | The user indicates whether he/she experienced nausea or vomit while he/she was in pain. |
| | Other symptoms | The user may select among: a) light sensitivity, b) sound sensitivity and c) odours sensitivity (3-dimension variable). |

TABLE 2-continued

Inputs from Incident Information

| | Information Type | Specifications |
|---|---|---|
| Actions | Painkillers | The user provides information about him/her taking or not painkillers to ease his/her pain. |
| | Bath | The user provides information about him/her taking a bath to ease his/her pain or not. |
| | Sleep | The user defines whether he/she slept to ease his/her pain. |
| | None | The user indicates that he/she has taken no action to relieve his/her pain. |
| | Other therapies | The user may enter other therapies/actions that he/she applied to relieve his/her pain. |
| | Pain intensity | The user informs about the intensity of his/her pain 2 hours after the relief-action (if he/she has taken any) on a scale of 1 to 10 (10 being the most intense pain). |

TABLE 3

Inputs from "Daily Form" Information

| | Information Type | Specifications |
|---|---|---|
| Physical conditions | Stress level | The user indicates how stressful his/her day was from 1 to 5 (5 being "highly stressful"). |
| | Depression level | The user evaluates if there was an event within his/her day that upset him/her and how much he/she was upset. The values vary between 1 and 5 (5 being "Highly depressed") |
| | Sleep | The user provides feedback regarding how many hours he/she has slept the night before and/or within the day. |
| | Sleep Quality | The user provides information about how well he/she had slept the night before on 1 to 5 scale (1-poor, 5-excellent). |
| Eating habits | Water | The user enters the number of glasses of water he/she has consumed within the day |
| | Skipped meals | The user provides information regarding his/her punctuality in meals (Y/N answer). |
| | Consumed foods/drinks | The user provides information regarding the foods/drinks he/she may have consumed within the day. The investigated factors are correlated to migraines and include: a) Ripened cheeses (such as cheddar, Emmentaler, Stilton, Brie, and Camembert), b) Junk Food, c) Caffeinated Beverages such as tea, coffee, or cola (and also how many cups he/she consumed), d) Alcohol - including red wine (and also how many drinks he/she has consumed), e) Sweets - including chocolate and f) Other foods that the user has discussed with his/her doctor that might affect his/her migraine (the user can fill in as many foods items as he/she wants). |
| Environmental aspects | Odours | The user indicates if he/she has been exposed to intense smells/odours such as strong perfume, pine scents and cinnamon |
| | Flickering lights/ screens | The user provides feedback regarding his/her exposure to flickering lights or screens and the number of hours he/she has worked with his/her computer. |
| Medical Aspects | Acute medication | If the user has mentioned in his/her profile that he/she takes acute medication right now, then he/she has to indicate if he/she has taken such a medication within the specific day |
| | Prescribed medication | If the user has mentioned in his/her profile that he/she takes prescribed medication, then he/she has to indicate if he/she has taken such a medication within the specific day and also if he/she took the medication as recommended. |
| | Menses | If the user is a female, then she also has to confirm the day of her menstruation cycle that she is currently in. |

2. Prediction Subsystem

FIG. 1 illustrates a summary of the inputs and outputs to the prediction subsystem. The inputs and outputs are also summarized below.

Input

The data necessary for the subsystem to identify a specific user's migraine causes/triggers $X_{1 \ldots n}$ and to foresee the probability of the user to get a migraine attack within the month are:

His/Her Username

His/Her Profile information. This information is used in order to find users with similar profiles as his/hers and combine his/her data (e.g., daily habits, migraine incidents, feedback, etc.) with the respective data coming from the users with similar profiles (e.g., see Table 1 above)

Information that the user provides at the end of his/her day through the "daily form" This information is related to how many and what type of activities, that according to the medical community usually trigger migraines, the user has experienced within the day (e.g., see Table 3 above). This is then used to calculate the migraine probability of the forecoming days and update the migraine pattern of the user.

The indication of having or not a migraine incident within the day of each daily form he/she has completed (see Table 2 above). This information is retrieved in a Boolean way (i.e., there is a stored incident or not for this user). If there is a migraine incident, the incident is stored in association with "labels" (i.e., metadata) related to the migraine causes/triggers of the migraine incident. More specifically, the labels correspond to migraine causes/triggers of the migraine incident experienced by the user/similar users in the past under the same conditions as those described in the daily information.

The data with respect to the daily habits and the migraine incidents of the users with similar profile information as his/hers (used for at least one migraine pattern initially created for the user).

User's feedback regarding possible past false alarms—when the foreseen migraine probability of the user in a specific day is above 50% but the user has not logged any migraine incident, the user is asked to confirm or reject the foreseen migraine or even a "tendency" to experience it (e.g., feeling of getting sick but taking an action to avoid it). In the last case, the prediction is characterized as true and the actions for avoiding are stored for future suggestions to the user.

Output

The output of the prediction subsystem is a list of key/value pairs. Each pair of values has the form of [date, probability of a migraine incident, factors that may trigger/cause the (foreseen) migraine]. The probability of a migraine incident is expressed as a percentage (i.e., there is x % risk of getting a migraine within dd/mm/yyyy due to migraine causes/triggers $X_{1 \ldots n}$). However, for simplicity reasons, in one embodiment, the first user interface informing the user of the probability to get a migraine attack is expressed in a monthly-based calendar view where a) the days during which the migraine risk is low (e.g., below 50%) are a first color (e.g., white), b) the days during which there is a low migraine risk (e.g., 50%-75%) are a second color (e.g., yellow) and c) the days during which the user will most probably experience a migraine (e.g., above 75%) are a third color (e.g., red). The user can get the exact probability and the migraine causes/triggers by selecting (clicking on) the day he/she is interested in.

Operation of Prediction Subsystem

The prediction subsystem is designed and developed so as to predict the user's next migraine attack. Specifically, the prediction subsystem correlates the user's (and, when necessary, the similar users') daily habits with his/her migraine incidents (i.e., creates his/her migraine pattern). For example, a possible migraine pattern could be that when the user has everyday more than 5 caffeinated beverages for 9 very stressful days in the row, the 10th day he/she gets a migraine attack. The subsystem is capable of identifying and learning such patterns and thus predicting the probability of the user to get a migraine attack within a period of time (e.g., the month) based on the user's/similar users' daily habits obtained from the daily information forms. When the system predicts a migraine, it displays to the user the associated migraine causes/triggers $X_{1 \ldots n}$, identified by the prediction subsystem from the user's/similar users' migraine patterns. The migraine causes/triggers $X_{1 \ldots n}$ correspond to migraine causes/triggers, that the medical community has identified (e.g., dehydration, consumption of particular foods, etc.), that applied in past migraine incidents experienced by the user (or similar users) under the same conditions as those described in the daily information form (i.e., the specific values of the daily habits in the daily information form). The subsystem generates a new prediction for a user when the user submits a new "daily form."

Algorithms

The prediction subsystem includes three main processes. More specifically, the subsystem uses a) Parameterless Growing Self-Organizing Maps (PLGSOM) for identifying similar (in terms of profile data) users, the data of whom may be latter exploited to enhance the performance of migraine predictions for a user that either has not provided enough data yet or whose data has changes, b) Deep Learning techniques for inferring the probability of the user to get a migraine and c) configuration management algorithms for processing the results and managing the configuration of PLGSOM and Deep Learning techniques in order to maximize their performance. Each of these processes is described in more detail below.

PLGSOM

When a user registers, his/her profile is classified among already registered user profiles based on PLGSOM technique, which is an unsupervised neural network clustering technique.

As a neural networks technique, PLGSOM mimics how human perception functions and thus, it is expected to be an adequate substitute of human processes.

Figure 2:
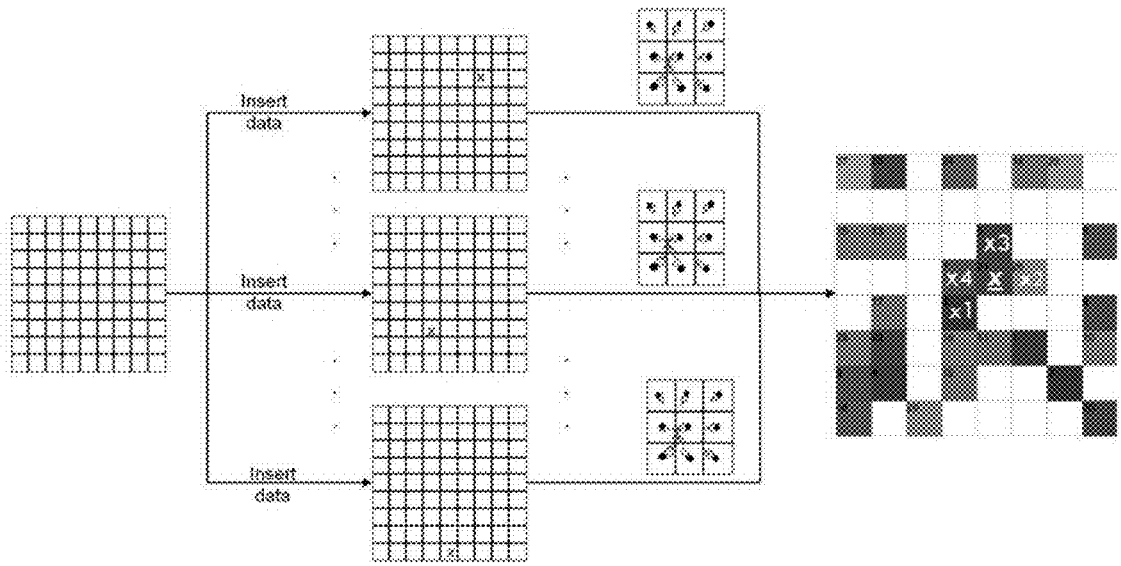
FIG. 2 is a block diagram that illustrates a pictorial representation of the construction of a Self-Organizing Map

A user's profile is classified by training a Self-Organized Map (SOM) in the PLGSOM technique, which is as follows:
1. The map, which is a grid of cells (see FIG. 2), is initialized by representing each of its cells with a vector that is comprised from as many components as the dimensions of the data, which are the variables of the user's profile in this case.
2. Each data sample (i.e., user profile) is expressed as a vector, the weights of which are equal to the values of the dimensions of the data sample, and is mapped on the cell whose vector is closest to it when using Euclidean distance (see FIG. 2).
3. The most important part is that the vectors of the data that are inserted to the training process of the map, also influence the weights of the map (cells) vectors so as to adjust them even closer to their weights.
4. The end of the training process finds the map complemented with the multi-dimensional data and split into clusters since the distance between the data samples is now represented by the distance between the cells of the map. In the context of this subsystem, the variables that relate to user profile are used for training the SOM, (i.e., for updating the weights of the cell vectors and thus, creating the clusters).

The outcome of this process is that users with similar profiles are grouped together (i.e., each user is classified with a cluster/group). The information as to which group a user belongs may or may not be exploited by the Deep Learning technique that builds the user's migraine pattern depending on how "mature" the user is. The "maturity" of the user depends on how much data (daily forms, migraine incidents, etc.) the user has entered and if there has been a recent change in his/her habits. Given the complexity and the individuality of the users, the configuration management algorithms described below have been set up to support results assessment and thus, configuration management (i.e., decisions regarding the use or not of PLGSOM outcomes and in general the exact configuration of the processes).

Deep Learning

The prediction subsystem uses deep neural networks to build a user's migraine pattern and predict the probability of future migraines given a user's daily information. More specifically, in the preferred embodiment, the system uses Deep Learning/LSTMs to build migraine patterns and make predictions.

Deep Learning techniques is a type of machine learning that uses lots of layers in a neural network to analyze data at different abstractions. In the preferred embodiment, given the type of the data (time series) and the need to predict future migraines, the neural network used in the layers of deep learning in the prediction subsystem is a Recurrent Neural Network (RNN), namely the "Long Short-Term Memory Units" (LSTMs).

Recurrent neural networks are used for time series data due to their memory capability (i.e., their capability to take into account both the current (t) and previous (t-1) timestamps when deciding on the next action). In one embodiment, each input example of the RNN is comprised of the variables in the daily information form, while the desired output of the subsystem is designated by the registration or not of a migraine incident by the user within the day.

The RNN is trained periodically using user data collected until the actual time of training. An input vector is created for each daily information form submitted by a user, and the corresponding output is whether a migraine incident was registered by the user. In one embodiment, multiple migraine patterns are created for a user, some based on the user's data alone and others based on both the user's data and the data of similar users, as determined by the PLGSOM process described above. Which of the user's migraine patterns is used for prediction is determined by the configuration management algorithms described below.

For patterns that involve both the user's and similar users' data, the nearest users' data are combined with the user's own data in order to create delimited files which then are fed into the RNN for training. It is worth clarifying here that the data of the nearest users which are used are also subject to filtering. For example, the number of the most similar users N is limited (e.g., to 9) and only the data of those who have submitted at least X "daily forms" (e.g., 5) and Y "migraine incidents" (e.g., 1) are used if the configuration management algorithms suggest that other users' data should be exploited. After the training phase, the migraine patterns created for each user are stored so as to be loaded when the prediction subsystem is triggered or for evaluation purposes of the model.

As soon as the user submits a "daily form", the subsystem exploits the provided data to create an RNN example data. Using this example data, the subsystem identifies similar example data within the user's migraine patterns. Based on these patterns, the subsystem receives feedback with respect to how close to a migraine incident the user is, and the deep learning process calculates the probability of reaching to a state where the user gets a migraine. The deep learning process also identifies the migraine causes/triggers $X_{1...n}$ (i.e., the daily information values) that lead to such state. The calculated probability is the migraine risk percentage that is returned to the user.

Configuration Management Algorithms

As already stated above, the results assessment and the configuration management (including the decisions of exploiting or not the outcomes of the PLGSOM process) are performed through the configuration management algorithms. More specifically, these algorithms are responsible for periodically (e.g., every week) self-evaluating the performance of the prediction subsystem and accordingly deciding its configuration. To this end, multiple configurations of the prediction subsystem are used to create multiple migraine patterns for each user. The configuration may refer to the training algorithm (e.g., adadelta, adagrad, rmsprop) of the deep learning technique, its training cycle, the timestamp used (time-window of the data), the use or not of the data coming from other users, etc. In order the configuration management algorithms to decide on the most appropriate configuration for each user, the migraine prediction subsystem initially calculates the migraine probability using all configurations and returns to the user the higher calculated probability. After the end of each "self-evaluating" period, the configuration management algorithms validate the performance of each configuration in terms of the percent of predicted migraines and false-positive insights based on the user's feedback and the submitted migraine incidents. The N configurations (e.g., at least 2) that scored higher are those that are used during the next period by the migraine prediction subsystem. Moreover, each time the user feedback reports a false positive insight, the migraine prediction subsystem returns the next lower probability (instead of the initially highest). On the contrary, each time a migraine is missed, the subsystem returns the next highest probability to the user. In the event that the performance of the prediction subsystem deteriorates in the latest "self-evaluating" period, the process translates this as a change in the user's migraine pattern and habits and re-initializes the process (i.e., all configurations will be used in the next "self-evaluation" period and will then be limited based on key performance indicators (KPIs.)

Use of Algorithms in Operation

FIGS. 3 and 9A-C illustrates how the above algorithms are used by the prediction subsystem to provide a personalized migraine prediction for a user. In response to receiving profile information from a new user, the system identifies other users in the system that are similar to the user by training a SOM neural map in accordance with PGLSOM techniques (steps 910, 920 in FIG. 9A). More specifically, the system uses the user's profile information and a SOM based on existing users to identify the user's cluster, and then creates a new SOM with both the existing users and the new user. As described below, the purpose of this is that the system will generate multiple migraine predictions for the user, some based on the user's data alone and some based on the combination of the user's data and the data of other users similar to the user.

Figure 9A:
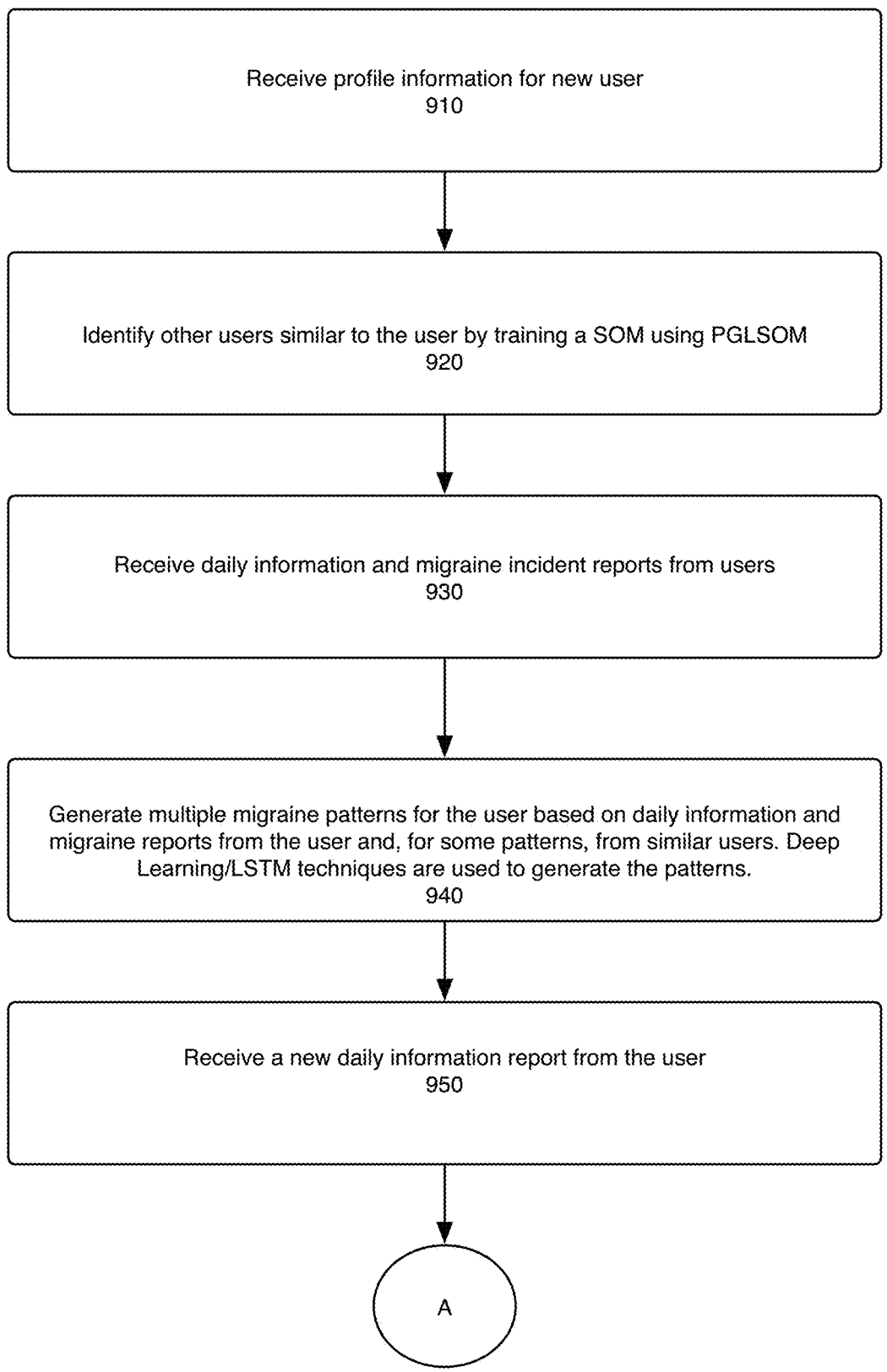
FIGS. 9A-C are flowcharts that illustrate the operation of the prediction subsystem.

The prediction subsystem uses the above-described Deep Learning techniques with a LSTM deep neural network to generate multiple migraine patterns for the user based on the daily information and migraine incident reports received from the user and, for some patterns, from similar users (as identified through the PGLSOM process) (steps 930, 940 in FIG. 9A). Each migraine pattern is based on an LSTM neural network that is trained with daily information and migraine incident report data and that is guided by Deep Learning techniques. Each migraine pattern corresponds to a different configuration of the prediction subsystem. As stated above, the configuration may refer to the training algorithm (e.g., adadelta, adagrad, rmsprop) of the deep learning technique, its training cycle, the timestamp used (time-window of the data), the use or not of the data coming from other users, etc. At least one migraine pattern is generated from the user's data alone, and at least one migraine pattern is generated using both the user's data and similar user's data.

Figure 9B:
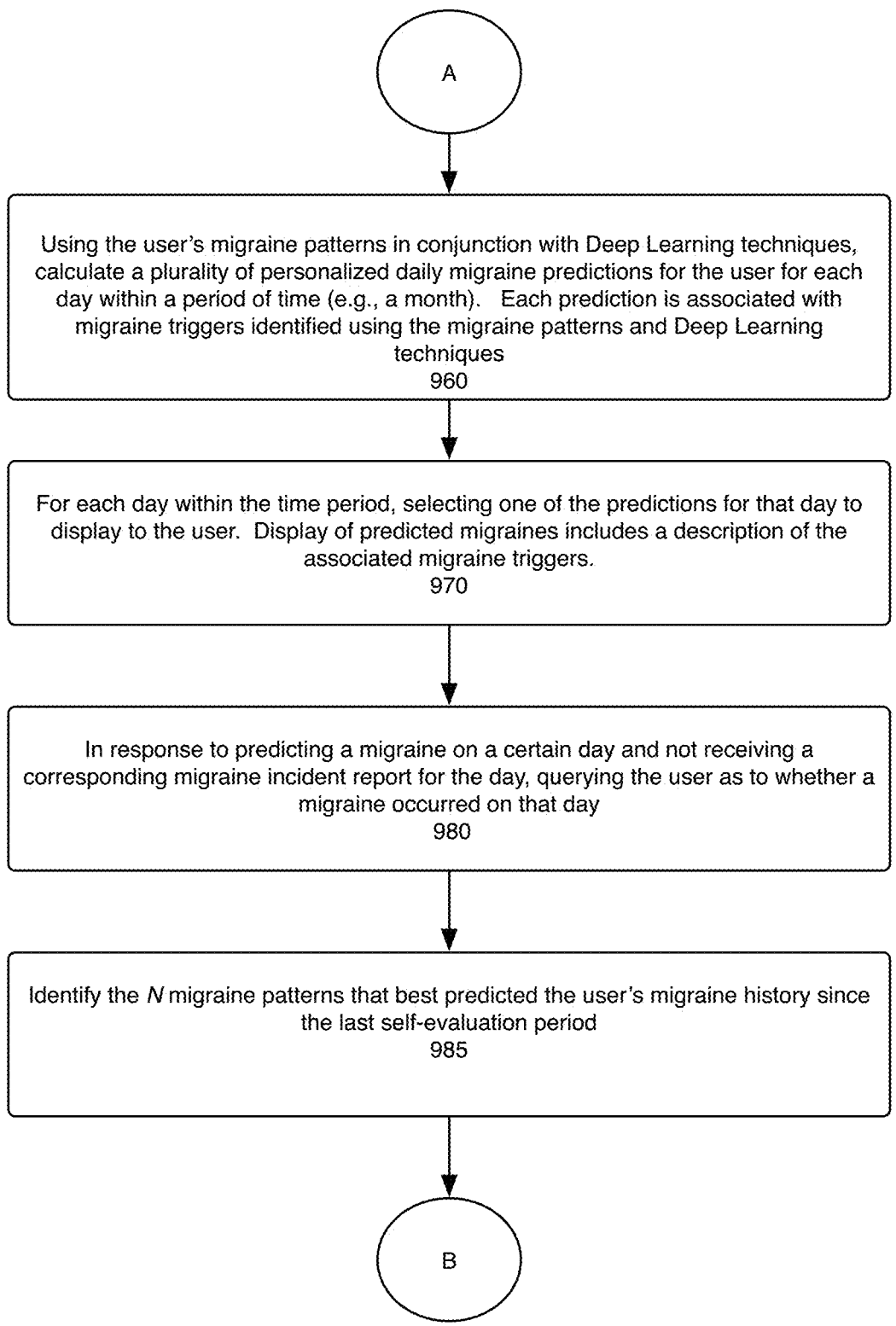
Figure 9C:
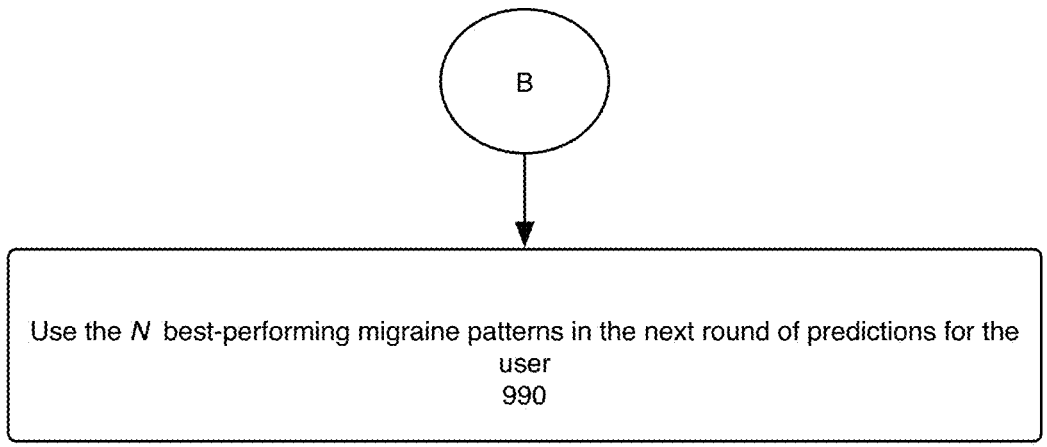

In response to the user submitting a daily information report, the subsystem uses the users' migraine patterns in conjunction with Deep Learning techniques to calculate a plurality of personalized daily migraine predictions for each day within a period of time (e.g., a month) (steps 950, 960 in FIGS. 9A-B). More specifically, the subsystem applies the new daily information (in the form of an input vector) to each of the user's migraine patterns (i.e., each LSTM trained for the user) and, for each pattern, receives an indication of how close the user is to a migraine state. For each of the migraine patterns, the system then uses Deep Learning processes to calculate the probability of the user reaching the migraine state and to identify the migraine triggers that lead the most probable migraine state.

Figure 3:
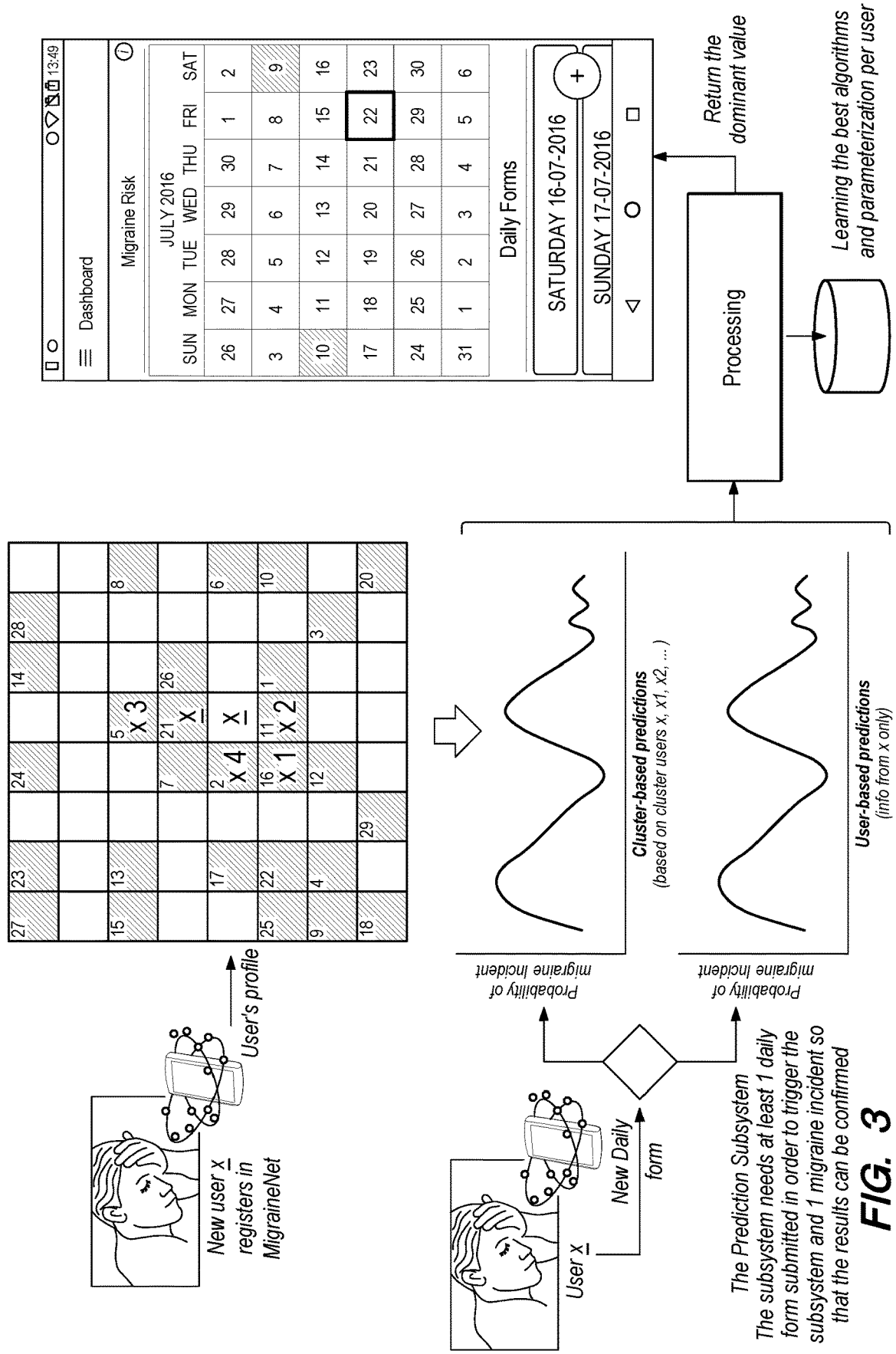
FIG. 3 is a flow diagram that illustrates the operation of the prediction subsystem according to one embodiment.
Figure 4:
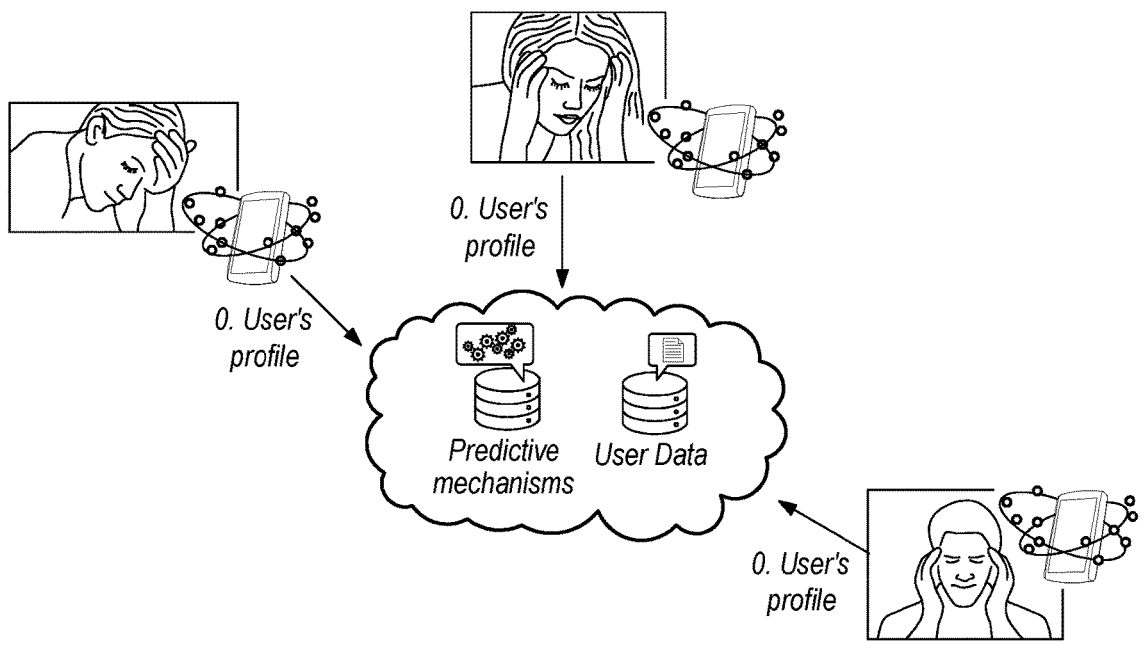
FIGS. 4-7 illustrates the workflow with respect to system/user exchange of data.
Figure 5:
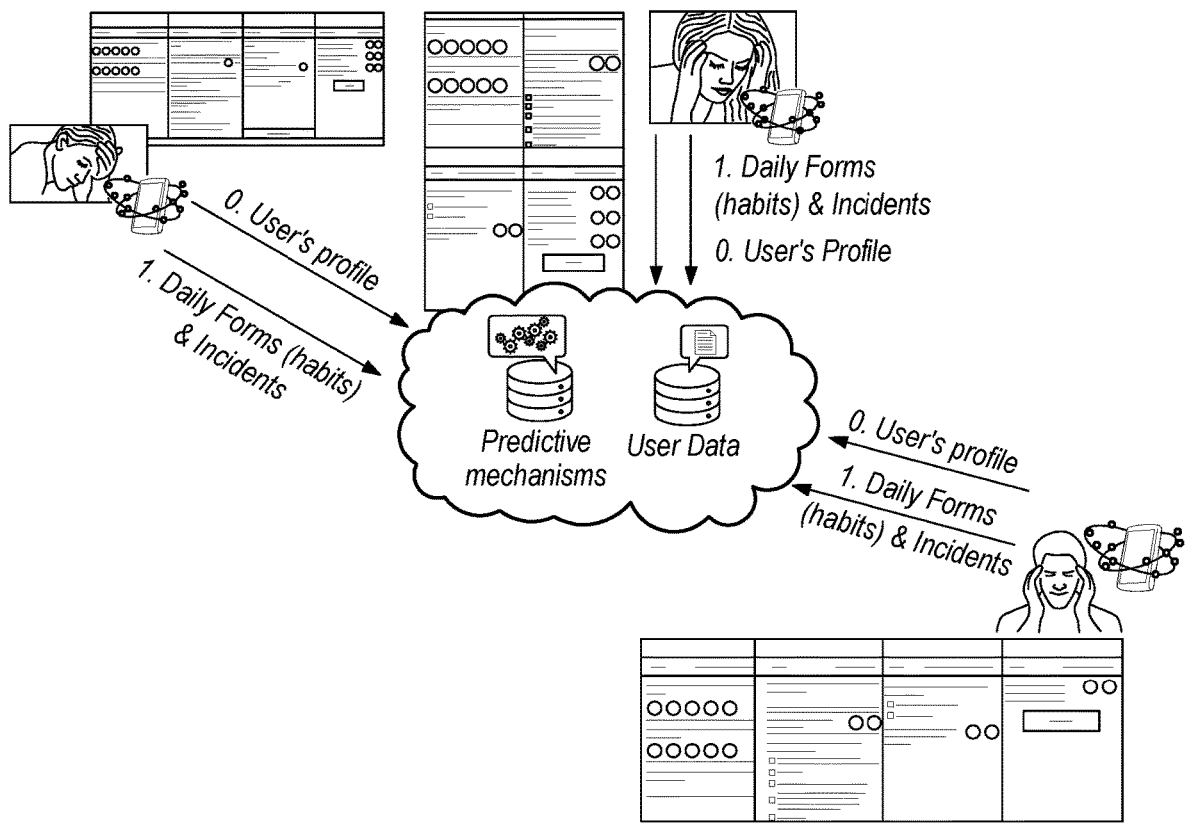
Figure 6:
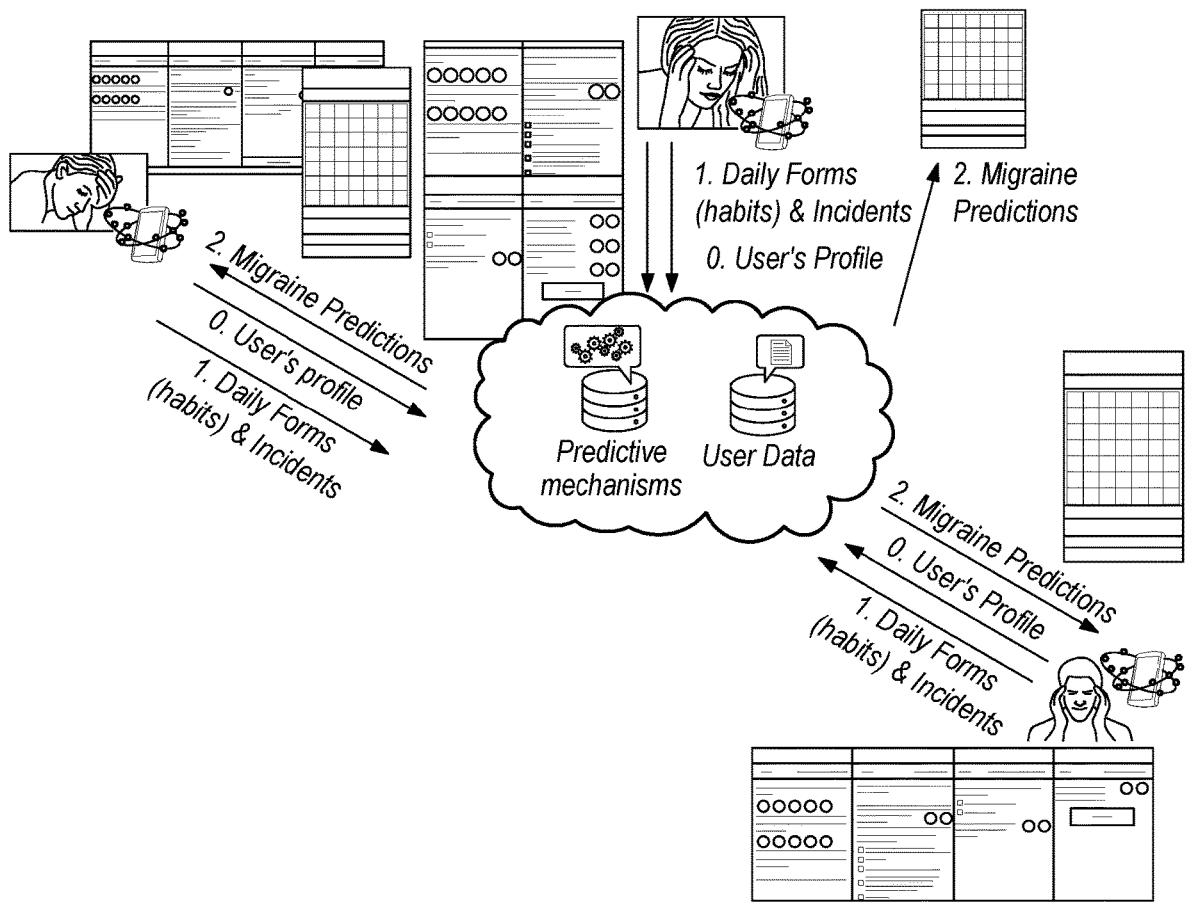

Step 960 results in multiple predictions for each day within the month (or other time period). This is because there is prediction corresponding to each of the migraine patterns created for the user in step 940. As shown in FIG. 3, there are user-based predictions and cluster-based predictions, as there are user-only migraine patterns and "user+ similar users" migraine patterns. The system will later assess which predictions were the most accurate in accordance with the configuration management algorithms.

For each day within the time period, the system selects one of the predictions for that day to display to the user (step 970 in FIG. 9B). As discussed above, the predictions may be displayed in the form of a color-coded calendar, where a user can click on a particular day to see the calculated migraine probability and, for days in which a migraine incident is probable (>50% chance), the associated migraine triggers that lead to the migraine prediction (see FIG. 3).

Initially, for each day, the system selects the prediction with the highest probability of a migraine to occur. The system may rely on different patterns on different days, as the migraine pattern that results in the highest probability of a migraine occurring may change depending on the day.

If the user subsequently reports a false positive prediction, the next time the system selects, for each day, the prediction with the next lower probability of the user having a migraine. Conversely, if the user reports a false negative, the next time the system selects, for each day, the prediction associated with the next higher probability of a migraine to occur. This continues until the configuration management algorithms in step 985.

If the prediction subsystem predicts a migraine (>50% probability or other threshold) on a certain day and does not receive a corresponding user report of a migraine incident, the system requests user feedback as to whether the predicted migraine occurred (step 980 in FIG. 9B).

Periodically (e.g., weekly), the prediction subsystem self-evaluates its prediction performance as described above with respect to the configuration management algorithms. Specifically, for each user, the subsystem identifies the N migraine patterns that best predicted the user's migraine history since the last self-evaluation period (e.g., over the past week) (step 985 in FIG. 9B). These N migraine patterns are then used for the next set of predictions for the user (step 990 in FIG. 9C). Consequently, in the next round of predictions, the configuration subsystem will generate N predictions for the user for each day in the next month (or other time period), and initially, for each day, select the highest of the N predictions to display to the user. Between evaluation periods, the prediction selected is adjusted in accordance with the false positive/false negative approaches discussed above. In the next run of the configuration management algorithms, the configuration system determines if the prediction performance deteriorated in the latest self-evaluation period. If so, the configuration system re-initializes the process, and all configurations of the subsystem will be used in the next rounds of predictions and the process will repeat, starting with step 940. If there is no deterioration in prediction performance, the system continues to use the same N configurations in the next round.

3. Work Flow for User/System Exchange

Figure 7:
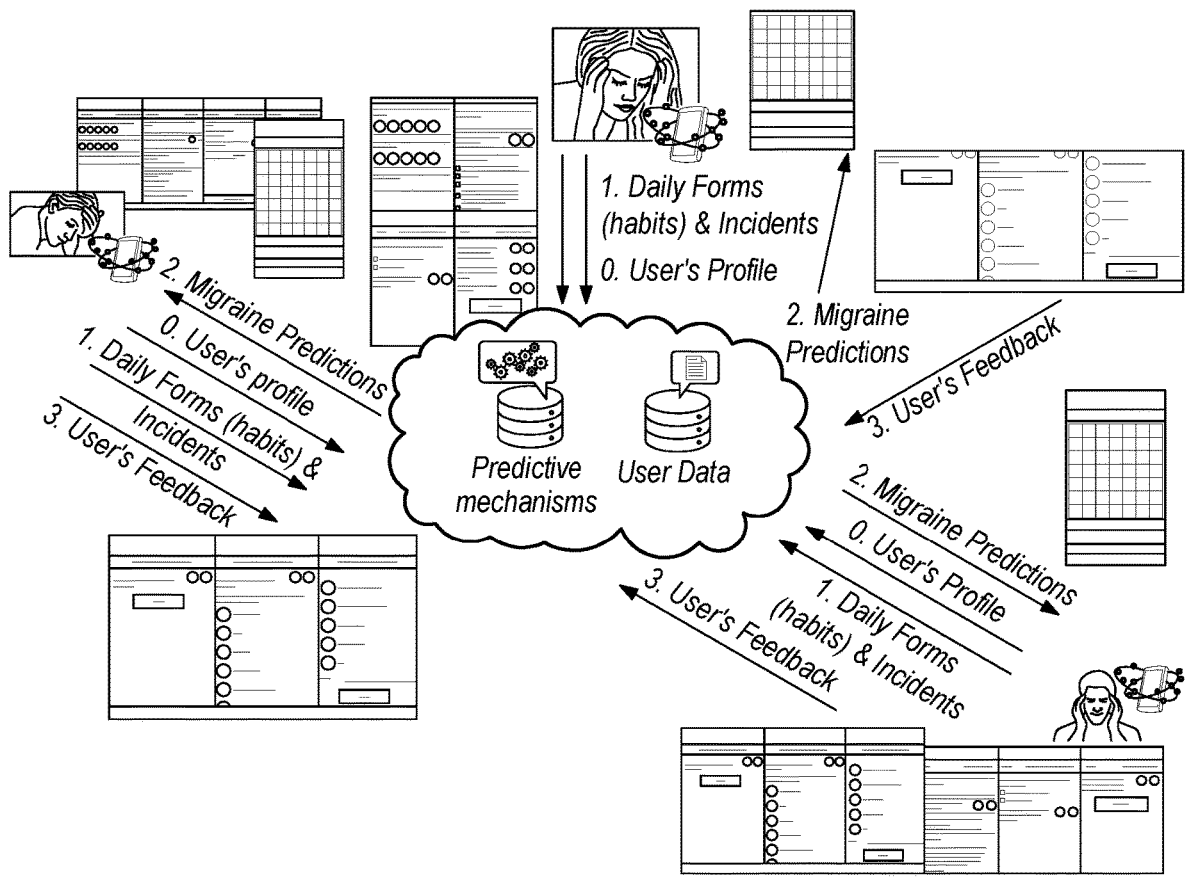

FIGS. 4-7 illustrates the workflow with respect to system/user exchange of data. In one embodiment, the system workflow comprises of four different steps:

- The registered users in the application provide their profile information in order for the prediction subsystem to identify users with similar profile information. (FIG. 4).
- The users provide their daily habits and register their migraine incidents (FIG. 5).
- The prediction subsystem is triggered by a daily form and calculates the personalized probability of a specific user to experience a migraine attack due to the migraine causes/triggers $X_{1 \ldots n}$ within the current month (FIG. 6).
- The user provides feedback concerning the accuracy of the prediction. This occurs when the invention returns a high probability of experiencing a migraine within the day but the user has not yet registered any migraine incident. In this case, the user needs to provide feedback whether he/she experienced migraine symptoms (and took actions to avoid the migraine) or there was a false positive. The system exploits the user's feedback in order to dynamically adjust the calculation of the migraine probabilities (FIG. 7).

4. System Architecture

Figure 8:
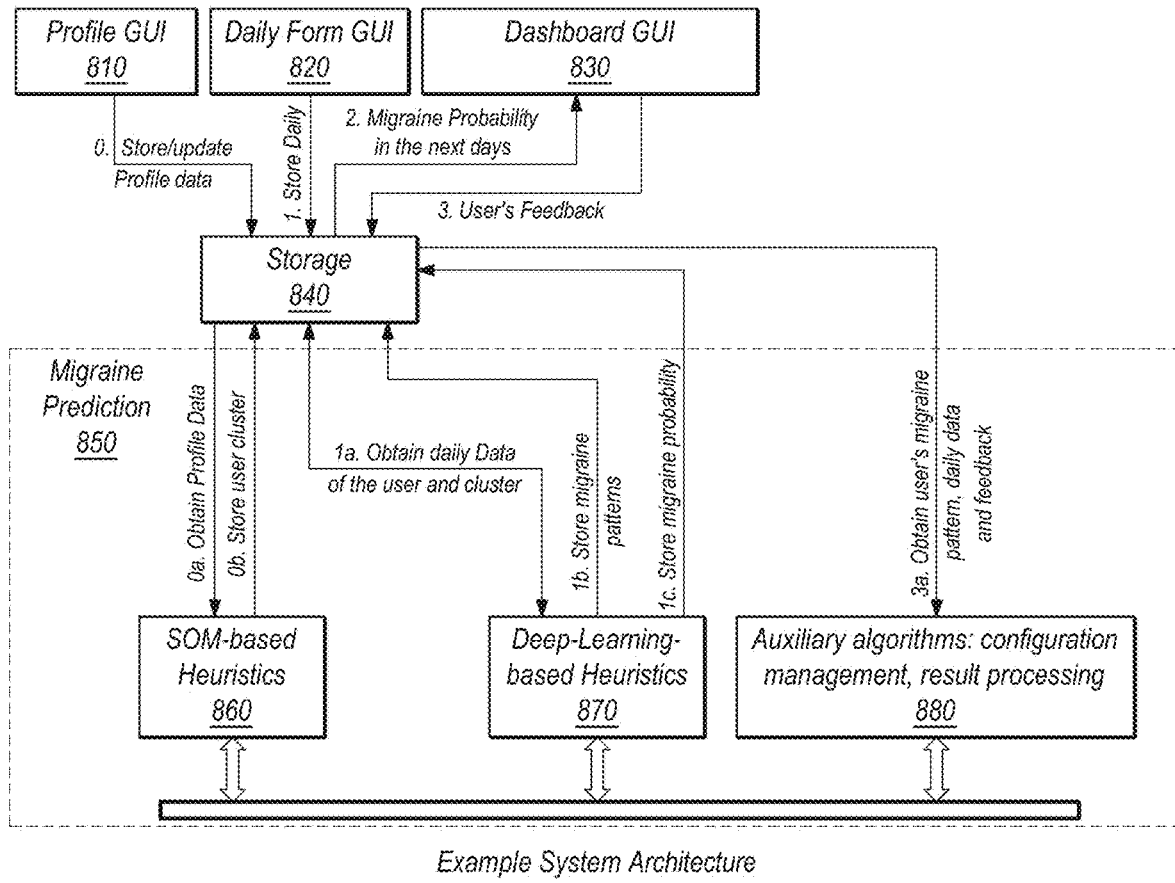
FIG. 8 is a block diagram that illustrates an example system architecture.

FIG. 8 illustrates an example system architecture. In one embodiment, the system comprises the following components:

- An application graphical user interface (GUI) that includes a Profile GUI 810, a Daily Form GUI 820, and a Dashboard GUI 830. A user views and interacts with the GUI on a client device, such as a laptop, tablet, or smart phone.
- A Storage component (840)
- The migraine prediction subsystem (840)

The GUI is used mainly for the communication with the user. Through this interface the user can a) enter his/her profile data when registering and update this information after the registration takes place; b) enter his/her daily habits (i.e., submit Daily Information forms); and c) register his/her migraine attacks (i.e., submit Migraine Incident forms). All the aforementioned information is stored in the Storage component 840 of the system, which acts as a middleware between the application GUI (810, 820, 830) and the Migraine prediction subsystem 850. The system may include both Web and mobile versions of the GUIs.

When a new user registers in the system, the user's profile data is retrieved from the Storage component 840, and subsequently the user's cluster is obtained by a SOM-based heuristic module 860 that uses the PGLSOM process described above. When a user completes a "daily form," this information and the daily information for the cluster that the user was allocated at after the registration process is obtained from the Storage component 840. These data are then fed into a Deep Learning-based heuristic module 870 that calculates the user's migraine patterns and also his/her probability, within a period of time, of having a migraine attack due migraine causes/triggers $X_1 \ldots _n$ identified through the Deep Learning/LSTM process described above. This probability as stated above, is stored as a key/value set where the key is the date and the values are the probability of having a migraine attack for this specific date and the associated migraine causes/triggers. This is also the probability returned to the user through the calendar view in the Dashboard GUI of the application 830. There, the user can assess his/her probability of having a migraine attack for each day of the current month. At this point it should be clarified that this probability is re-assessed when the user completes the next daily form or by the end of each "self-evaluating" period when a configuration management module 880 re-configures the parameterization of the Deep-Learning based Heuristics module 870 based on the user's feedback.

5. Alternate Embodiments

Below are some alternate ways in which the system may be implemented:

1. User are not clustered by profile information (i.e., steps 910 and 920 in FIG. 9A are omitted). Instead, all migraine patterns for a user are created based on the user's data alone.
2. For embodiments, in which users are clustered based on profile, different clustering techniques may be used instead of PGLSOM (e.g., k-means, neural gas, etc.).
3. Different types of machine learning techniques may be used instead of Deep Learning LSTM (e.g., ARMA, Exponential Smoothing, etc.).
4. Only one prediction is calculated for each day based on a single migraine pattern generated for the user. In this case, such prediction is the prediction displayed to the user.

6. General

The methods described herein are embodied in software and performed by a computer system (comprising one or more computing devices) executing the software. A person skilled in the art would understand that a computer system has one or more memory units, disks, or other physical, computer-readable storage media for storing software instructions, as well as one or more processors for executing the software instructions.

As will be understood by those familiar with the art, the invention may be embodied in other specific forms without departing from the spirit or essential characteristics thereof. Accordingly, the above disclosure is intended to be illustrative, but not limiting, of the scope of the invention, which is set forth in the following claims.

The invention claimed is:

1. A method, performed by a computer system, for predicting the likelihood that a user will have a migraine within the month due to a plurality of migraine triggers identified by the system, the method comprising:

receiving user profile information for users in the system;

clustering the users based on user profile information and identifying a plurality of users similar to the user, wherein clustering the users comprises creating a Self-Organizing Map (SOM) of users based on user profile information, wherein the SOM is created using Parameterless Growing Self-Organizing Map (PGLSOM) techniques;

receiving daily information and migraine incident reports from users in the system;

generating a plurality of migraine patterns for the user using deep neural networks, wherein at least one migraine pattern is based on only the user's daily information and migraine incident reports, and at least one migraine pattern is based on both the user's and the identified similar users' daily information and migraine incident reports;

in response to the user submitting a daily information report, using the migraine patterns to calculate a plurality of personalized migraine predictions for the user for each day in a period of time, wherein each prediction is associated with a probability and associated migraine triggers identified from the applicable migraine pattern;

for each day in the time period, selecting a prediction for that day to display to the user;

for each day, displaying the prediction selected for the day, wherein, for days in which a migraine probability exceeds a threshold, the associated migraine triggers for the prediction are also displayed;

in response to a probability associated with a migraine prediction exceeding a threshold on a certain day and not receiving a corresponding migraine incident report for that day, querying a user as to whether a migraine occurred on the day;

identifying the N migraine patterns that best predicted the user's migraine history during a self-evaluation period; and using the identified N migraine patterns for the next set of migraine predictions for the user.

2. The method of claim 1, wherein the migraine patterns are created by a prediction subsystem in the system, and each different migraine pattern created for a user corresponds to a different configuration of the prediction subsystem.

3. The method of claim 1, wherein the system uses Deep Learning techniques with a Long Short-Term Memory (LSTM) deep neural network to generate the migraine patterns, make migraine predictions, and identify the user's migraine triggers.

4. The method of claim 1, wherein the predictions for the time period are displayed in the form of a color-coded calendar, wherein, in response to the user clicking on a particular day within the time period, displaying the calculated migraine probability for the day.

5. The method of claim 4, further comprising displaying the associated migraine triggers in response to the probability for the day exceeding a threshold.

6. The method of claim 1, wherein the threshold is fifty percent.

7. The method of claim 1, wherein selecting a prediction for each day comprises:

initially, for each day in the time period, selecting the prediction for that day with the highest probability of a migraine to occur;

in response to the user subsequently reporting a false positive prediction, using a next lower probability prediction for each day in the next round of predictions; and in response to the user reporting a false negative prediction, using a next higher probability prediction for each day in the next round of predictions.

8. A non-transitory computer-readable medium comprising a computer program, that, when executed by a computer system, enables the computer system to perform the following method for predicting the likelihood that a user will have a migraine within the month due to a plurality of migraine triggers identified by the system, the method comprising:

receiving user profile information for users in the system;

clustering the users based on user profile information and identifying a plurality of users similar to the user, wherein clustering the users comprises creating a Self-Organizing Map (SOM) of users based on user profile information, wherein the SOM is created using Parameterless Growing Self-Organizing Map (PGLSOM) techniques;

receiving daily information and migraine incident reports from users in the system;

generating a plurality of migraine patterns for the user using deep neural networks, wherein at least one migraine pattern is based on only the user's daily information and migraine incident reports, and at least one migraine pattern is based on both the user's and the identified similar users' daily information and migraine incident reports;

in response to the user submitting a daily information report, using the migraine patterns to calculate a plurality of personalized migraine predictions for the user for each day in a period of time, wherein each prediction is associated with a probability and associated migraine triggers identified from the applicable migraine pattern;

for each day in the time period, selecting a prediction for that day to display to the user;

for each day, displaying the prediction selected for the day, wherein, for days in which a migraine probability exceeds a threshold, the associated migraine triggers for the prediction are also displayed;

in response to a probability associated with a migraine prediction exceeding a threshold on a certain day and not receiving a corresponding migraine incident report for that day, querying a user as to whether a migraine occurred on the day;

identifying the N migraine patterns that best predicted the user's migraine history during a self-evaluation period; and using the identified N migraine patterns for the next set of migraine predictions for the user.

9. The non-transitory computer-readable medium of claim 8, wherein the migraine patterns are created by a prediction subsystem in the system, and each different migraine pattern created for a user corresponds to a different configuration of the prediction subsystem.

10. The non-transitory computer-readable medium of claim 8, wherein the system uses Deep Learning techniques with a Long Short-Term Memory (LSTM), deep neural network to generate the migraine patterns, make migraine predictions, and identify the user's migraine triggers.

11. The non-transitory computer-readable medium of claim 8, wherein the predictions for the time period are displayed in the form of a color-coded calendar, wherein, in response to the user clicking on a particular day within the time period, displaying the calculated migraine probability for the day.

12. The non-transitory computer-readable medium of claim 11, further comprising displaying the associated migraine triggers in response to the probability for the day exceeding a threshold.

13. The non-transitory computer-readable medium of claim 8, wherein the threshold is fifty percent.

14. The non-transitory computer-readable medium of claim 8, wherein selecting a prediction for each day comprises:

initially, for each day in the time period, selecting the prediction for that day with the highest probability of a migraine to occur;

in response to the user subsequently reporting a false positive prediction, using a next lower probability prediction for each day in the next round of predictions; and in response to the user reporting a false negative prediction, using a next higher probability prediction for each day in the next round of predictions.

15. A computer system for predicting the likelihood that a user will have a migraine within the month due to a plurality of migraine triggers identified by the system, the system comprising:

one or more processors;

one or more memory units coupled to the one or more processors, wherein the one or more memory units store instructions that, when executed by the one or more processors, cause the system to perform the operations of:

receiving user profile information for users in the system;

clustering the users based on user profile information and identifying a plurality of users similar to the user, wherein clustering the users comprises creating a Self-Organizing Map (SOM) of users based on user profile information, wherein the SOM is created using Parameterless Growing Self-Organizing Map (PGLSOM) techniques;

receiving daily information and migraine incident reports from users in the system;

generating a plurality of migraine patterns for the user using deep neural networks, wherein at least one migraine pattern is based on only the user's daily information and migraine incident reports, and at least one migraine pattern is based on both the user's and the identified similar users' daily information and migraine incident reports;

in response to the user submitting a daily information report, using the migraine patterns to calculate a plurality of personalized migraine predictions for the user for each day in a period of time, wherein each prediction is associated with a probability and associated migraine triggers identified from the applicable migraine pattern;

for each day in the time period, selecting a prediction for that day to display to the user;

for each day, displaying the prediction selected for the day, wherein, for days in which a migraine probability exceeds a threshold, the associated migraine triggers for the prediction are also displayed;

in response to a probability associated with a migraine prediction exceeding a threshold on a certain day and not receiving a corresponding migraine incident report for that day, querying a user as to whether a migraine occurred on the day;

identifying the N migraine patterns that best predicted the user's migraine history during a self-evaluation period; and using the identified N migraine patterns for the next set of migraine predictions for the user.

16. The system of claim 15, wherein the migraine patterns are created by a prediction subsystem in the system, and each different migraine pattern created for a user corresponds to a different configuration of the prediction subsystem.

17. The system of claim 15, wherein the system uses Deep Learning techniques with a Long Short-Term Memory (LSTM) deep neural network to generate the migraine patterns, make migraine predictions, and identify the user's migraine triggers.

18. The system of claim 15, wherein the predictions for the time period are displayed in the form of a color-coded calendar, wherein, in response to the user clicking on a particular day within the time period, displaying the calculated migraine probability for the day.

19. The system of claim 18, further comprising displaying the associated migraine triggers in response to the probability for the day exceeding a threshold.

20. The system of claim 15, wherein the threshold is fifty percent.

21. The system of claim 15, wherein selecting a prediction for each day comprises:
- initially, for each day in the time period, selecting the prediction for that day with the highest probability of a migraine to occur;
- in response to the user subsequently reporting a false positive prediction, using a next lower probability prediction for each day in the next round of predictions; and
- in response to the user reporting a false negative prediction, using a next higher probability prediction for each day in the next round of predictions.

* * * * *